United States Patent [19]

Gardner

[11] Patent Number: 5,267,952
[45] Date of Patent: Dec. 7, 1993

[54] BANDAGE WITH TRANSVERSE SLITS

[75] Inventor: Arthur M. N. Gardner, Devon, United Kingdom

[73] Assignee: Novamedix, Ltd., Andover, United Kingdom

[21] Appl. No.: 952,344

[22] Filed: Sep. 28, 1992

[30] Foreign Application Priority Data

Dec. 24, 1991 [WO] PCT Int'l
 Appl. .................. PCT/GB91/02321

[51] Int. Cl.$^5$ ...................... A61F 13/00; A61F 15/00; A61L 13/00
[52] U.S. Cl. ......................................... 602/58; 602/41; 602/62; 602/63; 602/75; 128/854; 2/6; 2/22
[58] Field of Search ....................... 602/41, 42, 62, 65, 602/72, 75, 76, 77, 55, 900, 63; 128/854, DIG. 15; 2/2, 16, 22, DIG. 1

[56] References Cited

U.S. PATENT DOCUMENTS

| 2,096,564 | 10/1937 | Scholl | 602/75 |
| 3,255,749 | 6/1966 | Smithers | 602/77 |
| 4,534,354 | 8/1985 | Bonner, Jr. et al. | 602/75 |
| 4,699,134 | 10/1987 | Samuelson | 602/42 |
| 4,738,662 | 4/1988 | Kalt et al. | 128/DIG. 15 |
| 4,926,848 | 5/1990 | Shimkus et al. | 602/75 |
| 5,036,838 | 8/1991 | Sherman | 602/44 |
| 5,133,775 | 7/1992 | Chen | 2/16 |

FOREIGN PATENT DOCUMENTS 2268504 11/1975 France .................... 606/215

Primary Examiner—Randall L. Green
Assistant Examiner—Paul Prebilic
Attorney, Agent, or Firm—Hopgood, Calimafde, Kalil, Blaustein & Judlowe

[57] ABSTRACT

An elongate bandage that is predominantly stretchable in the longitudinal direction enables readily applied development of an elastic surgical limb sleeve that can be rendered locally inextensible. The bandage features multiple longitudinally spaced rows of transverse slits which are in staggered offsetting interlace, from one to the next-adjacent row, such that when a circumferential wrap of the bandage completes a sleeve, the multiple slits are arrayed parallel to the axis of the limb. The limb sleeve gently conforms to the shape of an affected or injured joint or other body part, and the gentle conformance is operative to convert slits into ventilation openings. One or more strips of relatively inelastic hook material applied to the outer surface of a developed sleeve not only complete the sleeve but, when desired by the surgeon, can exert localized pressure to the injured area either directly or indirectly as in the treatment of swelling or in the control of bleeding.

12 Claims, 2 Drawing Sheets

BANDAGE WITH TRANSVERSE SLITS

BACKGROUND OF THE INVENTION

This invention relates to bandages. In particular, it relates to a bandage which provides flexibility of use and extended scope of application over bandages presently available.

Existing bandages are typically in the form of a strip which is stored in a roll, or in the form of a tube. The tube may be shaped to conform to the particular location at which it is to be used, for example at the ankle joint. A tube, or sleeve, is generally a more convenient form than a strip since it is quick and relatively easy to apply, although its shape and size limit the scope of application.

Depending on the circumstances of use, a sleeve, in particular, may suffer the following disadvantages:

(i) it may be unduly restrictive to movement in a certain direction in which free movement is preferable;

(ii) it may not provide sufficient support, allowing too much movement in a certain direction or directions in which restricted movement is preferable;

(iii) it may be uncomfortable and, in particular, may not fit adequately;

(iv) it may tend to kink when the joint is flexed; or (v) it may cover an area which needs to remain open or accessible, such as a wound or bed sore.

According to the invention, there is provided a bandage having a first member comprising an elastic layer covered on at least one surface by a woven material, and a second member comprising a base material with upstanding hooked elements, the hooked elements of the second member engaging the woven material of the first member; wherein the first member has lines or areas of weakness and the base material of the second member is less elastic than the first member.

The first member may be easily extensible and the lines or areas of weakness may be local in extent. Such lines or areas of weakness provide means for controlling the stretching of the first member in diverse local areas and in specific directions according to the requirements of a particular application. Lines or areas of weakness are preferably slits or cuts only partially through the first member, but may be made through the entire thickness of the first member. The lines or areas of weakness may be introduced in situ and/or during manufacture. Lines of weakness are preferably generally parallel to the longitudinal axis of the limb to be bandaged. The bandage may thus be adapted to allow easy movement in specific areas and in specific directions since the first member will stretch in a direction generally normal to each slit. The use of a series of lines of weakness in the form of a lattice allows stretching in all directions.

In a preferred embodiment, the areas of weakness may be apertures which allow access to a wound site, for example, or which prevent wrinkling of the bandage during flexing of a joint.

BRIEF STATEMENT OF THE INVENTION

Preferably, the second member provides means for fastening the bandage when the hooked elements engage with the woven material of the first member. More preferably, one or more pieces of the second member may be used to strengthen the bandage by limiting or preventing stretching of the first member. One or more pieces of the second member may also be used to seal unwanted lines or areas of weakness in the first member.

The elastic layer is preferably of neoprene or similar material. The woven material is preferably attached to the elastic layer by adhesive, although alternative methods, such as heat sealing for example, may be used.

Still more preferably, means for holding inserts in position may be provided. The means may be pockets in the woven material which can hold inserts such as protective pads and plates, or inflatable pads for use with impulse-compression pads for local treatment of joints or tissues or activation of physiological venous pumps, e.g. of the hand, foot, calf, knee or thigh.

Alternatively, inserts may be located by positioning the inserts next to the first member and fixing in place by one or more pieces of the second member. In this manner inserts may be located on either side of the first member as required.

The bandage is suitably manufactured in the form of a sheet, but preferably it is in the form of a tubular bandage of a particular joint shape. Strips of bandage may be obtained by cutting a sheet into the required length and/or width. Tubular bandages may also be made in situ by sealing the ends of a sheet of the first member with one or more strips of the second member. A sheet may thus be closed by the one or more strips of the second member so as to form a cylinder. In this tubular configuration, the first member has a plurality of rows of slits which extend axially and wherein the rows are spaced circumferentially. The slits in each row correspond in axial length and in axial spacing.

The bandage may have an adhesive layer on part or all of at least one surface of the first member. Such an adhesive layer would improve protection of damaged ligaments or structural tissue by adhering to the skin surface.

According to a further aspect of the invention, there is provided a method of manufacturing a bandage comprising: manufacturing a first member by providing a layer of elastic material, attaching a layer of woven material on at least one surface of the layer of elastic material, and cutting slits through part or all of the first member thus formed; providing one or more pieces of a second member which is less elastic than the first member; and fastening the one or more pieces of the second member to the first member by engaging hooked elements on the second member with the woven material of the first member.

Applications of the bandage the subject of the invention include:

(i) Circumstances where support is required, such as in the protection of damaged ligaments, where appropriately positioned inhibition means can be used;

(ii) to hold impulse-compression pads inside a tubular bandage for local treatment of joints and tissues;

(iii) where rapid and unskilled placement of dressings with localised pressure is required, such as for preventing the bleeding of a wound in an emergency;

(iv) where ventilation of pressure sores or relief of pressure is required; and (v) in the construction of an immobilisation cast for body or limb, with the addition of a quick-setting material such as an alginate or plaster of Paris.

The thickness of the bandage is not critical to the invention since it should be suited to the particular material used and the specific application envisaged. A typical useful thickness is from 1.5 mm to 8 mm.

The numbers, sizes, shapes, locations, orientations and degrees of the areas of elastic inhibition and assistance govern the shape and characteristics of the bandage so that the bandage can be tailor-made for a specific application. Thus a bandage can be manufactured for application, not only for a particular site, but also for a particular purpose, and applied with speed and ease even by an unskilled person. Likewise, a bandage can be altered or adjusted before or during fitting to suit a special requirement. The bandage should conform to the particular application in that it must not compromise circulation.

The bandage and/or inhibition means may be colour-coded to indicate the degree to which they are elastic.

BRIEF DESCRIPTION OF THE DRAWINGS

The invention will now be described by way of example with reference to the accompanying drawings, in which.

DETAILED DESCRIPTION

Figure 1:
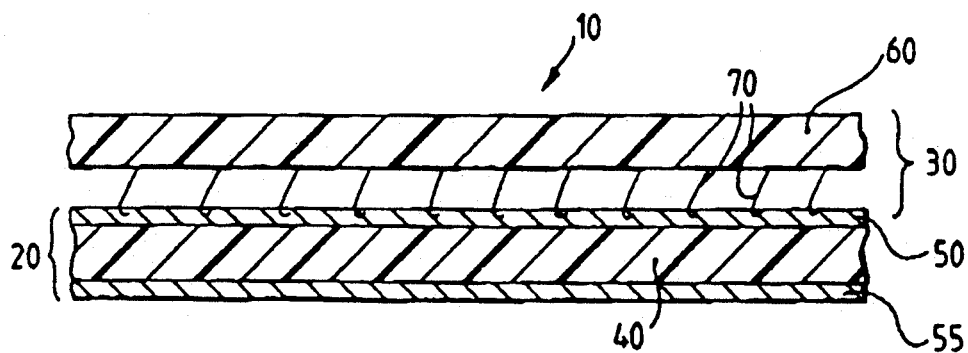
FIG. 1 is a schematic transverse section of a bandage according to the invention.

In FIG. 1, there is shown a bandage 10 comprising a first member 20 and a second member 30. The first member 20 has a layer 40 with a covering layer on each side. The covering layer on one side provides a comfort layer 55 for contact with the body and may also be used for location of inflation pads by a further second member. The covering layer 50 on the other side is engaged by hooked elements 70 extending from layer 60 of the second member 30. Layer 40 is an elastic material such as neoprene with covering layers 50 and 55 being woven material. In use the woven material 50, 55 is attached to the elastic material 40 during manufacture, by adhesive for example, so that the first member 20 can be stretched around the part of the body to be bandaged.

Layer 60 is less elastic than the first member or may be inelastic, being a moulded plastics material for example. In use, the hooked elements 70 engage the woven material 50, preventing stretching of first member 20 at the points of attachment.

Figure 2:
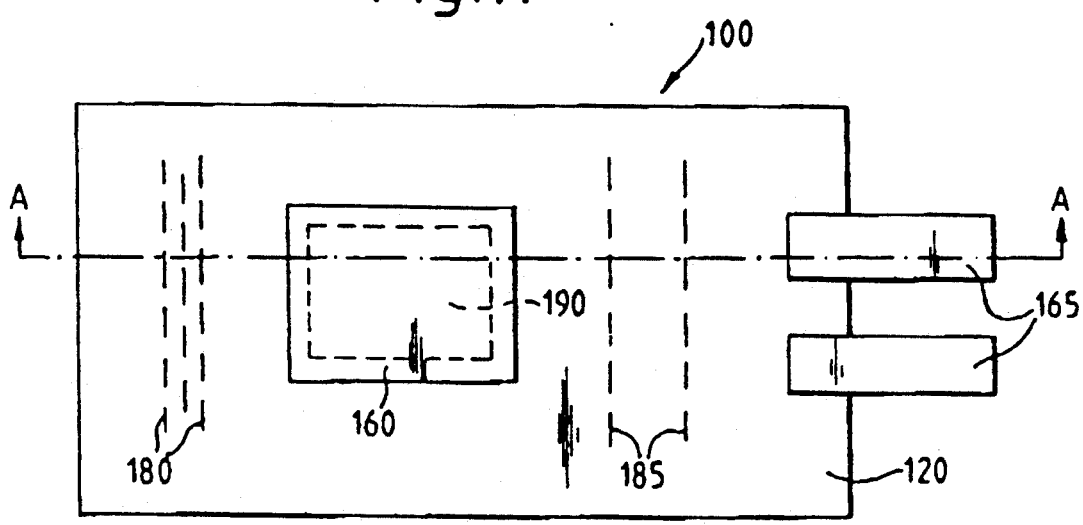
FIG. 2 is a schematic plan view of another bandage according to the invention.
Figure 3:
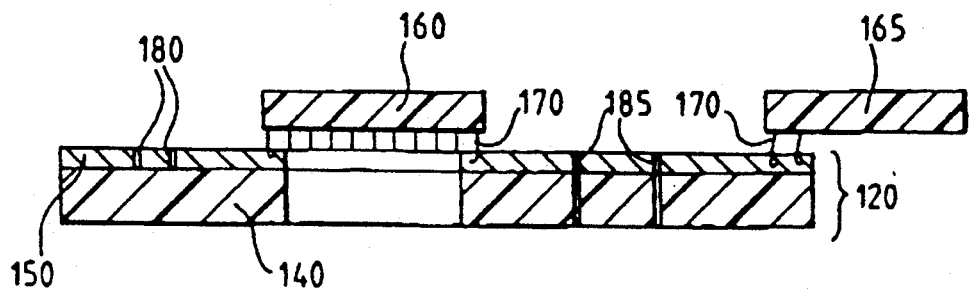
FIG. 3 is a schematic transverse section of the bandage of FIG. 2 viewed in direction A—A.

FIGS. 2 and 3 show an embodiment in which a bandage 100 has slits 180, 185 cut in its first member 120, and an aperture 190. Slits 180 are partial thickness, being cut through the woven material 150 only. Slits 185 are full thickness, being cut through both layers of the first member 120, comprising woven material 150 and elastic material 140 only in this embodiment.

Strips of inelastic material 165 are provided for securing the bandage and pieces of inelastic material 160 are placed around the aperture 190 so as to provide a local inelastic region which prevents unwanted deformation of the bandage.

Second member pieces 160, 165 may be Velcro (registered trade mark) or other similar inelastic material having hooked elements. The first member is, for example, wetsuit material, which may be 3 mm neoprene lined with a 0.5 mm thick woven material. It will be appreciated that other materials could be used. In particular woven material 150 could be a piled fabric, such as plush, or could have looped elements which engage with the hooked elements 170.

In use, sheets of bandage 100 are placed around the part of the body to be bandaged and are secured in place by strips of inelastic material 165. Slits 180 in the sheet provide lines of weakening, so that the sheet stretches generally normal to these lines. Instead of being manufactured as a sheet, the bandage may be manufactured in the form of a tube. In this case, slits are provided around arcs of the circumference of inelastic material. Unwanted slits may be sealed by strips of pieces of inelastic material. Further strips of inelastic material may be positioned where extra support or strengthening is required, such as along damaged ligaments or across incompletely healed fractures.

This example uses inelastic material for securing or strengthening, but it is possible to use material which is less elastic than that of the first member.

Figure 4:
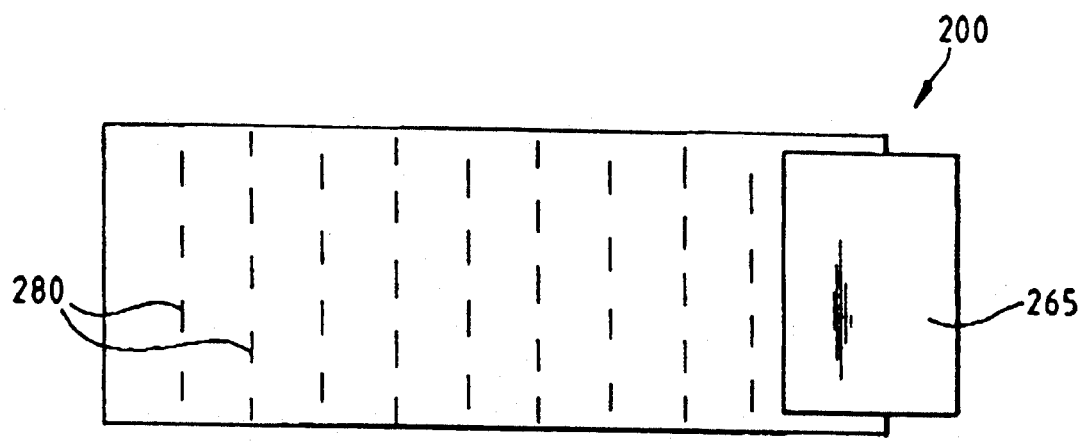
FIG. 4 is a schematic plan view of a further bandage according to the invention.
Figure 5:
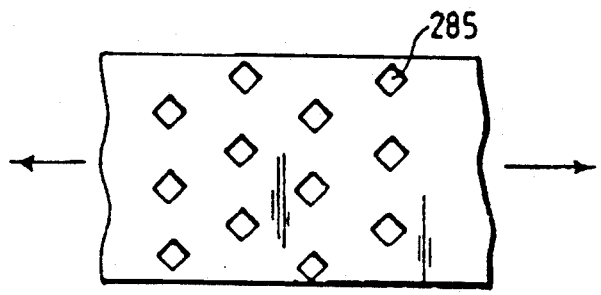
FIG. 5 is a schematic plan view of a stretched section of the bandage of FIG. 4.

In practice, the more preferred form of the bandage 200 would have multiple slits 280 in a "bricked" layout, as shown in FIG. 4. These slits 280 deform when stretched around a limb during application as shown in FIG. 5. The multiple slits become a lattice of diamond shapes 285 when stretched as indicated by the arrows. The use of this form enables stretching in all directions. Improved stretching is thereby achieved over the whole of the lattice region, the slits in each row corresponding in length and in transverse spacing, and the slits of one row being in staggered offsetting interlace with the slits of an adjacent row. The bandage 200 may be closed by a longitudinal strip of the second member 265 to form a tubular bandage.

The slits are generally closely spaced along the longitudinal axis of the limb to be supported. This weakens the force exerted by the first member so that by itself it exerts only minor constricting force to the limb.

Figure 6:
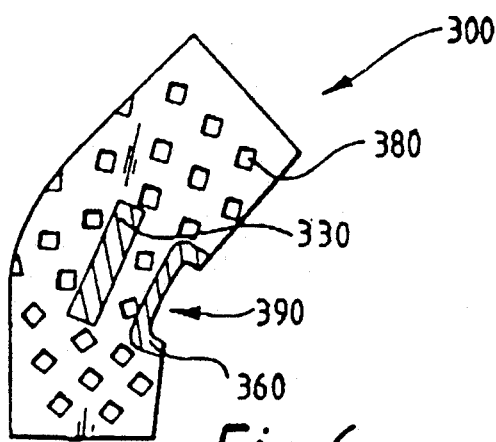
FIG. 6 is a schematic side view of a yet further bandage according to the invention.

FIG. 6 shows an embodiment in which the bandage has been manufactured in the form of a tubular support bandage 300 and shaped to conform to a knee joint. Slits 380 have been cut in the region where stretching of the bandage is required and have deformed to a diamond lattice. Further support to ligaments, for instance, is provided in the form of inelastic or less elastic regions obtained by the addition of strips of the second member 330. If necessary, an aperture 390 can prevent wrinkling of the bandage, the aperture being maintained in shape by a piece of the second member 360. The strips 330 may also be used to close a slit 380 if it is not required.

A versatile bandage and method of manufacturing a bandage have thus been provided which provide quick and easy application without the requirement of a large range of custom-fit bandages. It will of course be understood that the present invention has been described purely by way of example, and modifications can be made within the scope of the invention.

I claim:

1. A bandage of releasably engageable members, wherein a first member comprises an elongate composite sheet of elastic material covered on at least one surface by a woven material, and wherein a second member comprises a flexible-sheet base material having upstanding hooked elements, the weave of said woven material being adapted for selectively removable engagement of said hooked elements thereto, said composite sheet having a longitudinal dimension which exceeds its width dimension, and said composite sheet having a plurality of longitudinally spaced rows of slits which extend in the width direction, the slits in each row corresponding in length and in transverse spacing, and the slits of one row being in staggered offsetting interlace with the slits of a row adjacent to said one row.

2. The bandage of claim 1, wherein said composite sheet is the product of laminating said elastic material and said woven material to each other, and wherein said slits extend fully through both of the materials of said first member.

3. The bandage of claim 1, wherein said composite sheet is the product of laminating said elastic material and said woven material to each other, and wherein said slits extend only partially through said composite sheet.

4. The bandage of claim 1, wherein the base material of said second member is less elastic than said first member.

5. The bandage of claim 1, wherein said first member is generally rectangular.

6. The bandage of claim 5, wherein the base material of said second member is less elastic than said first member, whereby said second member can be selectively locally applied to woven material of said first member, thus locally restricting stretchability of said first member.

7. The bandage of claim 1, wherein an opposite surface of said first member is also covered with a woven material.

8. The bandage of claim 1, wherein said first member further includes a pocket for containment of an insert.

9. The bandage of claim 1, wherein said first member is in the form of a tube.

10. The bandage of claim 1, wherein the elastic material of said first member is neoprene.

11. The bandage of claim 1, wherein at least one surface of the first member is coated with adhesive.

12. A tubular bandage made from a composite sheet of first and second flexible releasably engageable members, said sheet being adapted to be closed by in situ sealing the ends of the sheet so as to form a cylinder having axial and circumferential dimensions in bandaged application to a particular joint shape around an injured limb, said first member comprising a layer of elastic material covered on at least one surface by a woven material, said second member comprising a flexible-sheet base material having upstanding hooked elements, the weave of said woven material being adapted for selectively removable engagement of said hooked elements thereto, and said first member having a plurality of rows of slits (a) which extend axially and (b) wherein the rows are spaced circumferentially, the slits in each row corresponding in axial length and in axial spacing, and the slits of one row being in staggered offsetting interlace with the slits of a row adjacent to said one row.

* * * * *